US008563531B2

(12) United States Patent
Ostroff et al.

(10) Patent No.: US 8,563,531 B2
(45) Date of Patent: Oct. 22, 2013

(54) METHODS OF USING BETA GLUCAN AS A RADIOPROTECTIVE AGENT (75) Inventors: Gary R. Ostroff, Worcester, MA (US); Gordon D. Ross, Prospect, KY (US); Trunetta Jo Dockter Ross, legal representative, Prospect, KY (US)

(73) Assignees: Biothera, Inc., Eagan, MN (US); University of Louisville Research Foundation, Inc., Louisville, KY (US)

( * ) Notice: Subject to any disclaimer, the term of this patent is extended or adjusted under 35 U.S.C. 154(b) by 878 days.

(21) Appl. No.: 12/217,701

(22) Filed: Jul. 8, 2008

(65) Prior Publication Data

US 2009/0163439 A1 Jun. 25, 2009

Related U.S. Application Data

(63) Continuation of application No. 11/057,102, filed on Feb. 11, 2005, now abandoned, which is a continuation of application No. PCT/US03/25237, filed on Aug. 13, 2003.

(60) Provisional application No. 60/403,424, filed on Aug. 13, 2002.

(51) Int. Cl.
*A01N 43/04* (2006.01)
*A61K 31/715* (2006.01)

(52) U.S. Cl.
USPC .......................................................... 514/54

(58) Field of Classification Search
None
See application file for complete search history.

(56) References Cited

U.S. PATENT DOCUMENTS

| 3,903,297 | A | 9/1975 | Robert |
|---|---|---|---|
| 3,943,247 | A | 3/1976 | Komatsu et al. |
| 4,138,479 | A | 2/1979 | Truscheit et al. |
| 4,237,266 | A | 12/1980 | Sugiura et al. |
| 4,492,540 | A | 1/1985 | Yamamoto |
| 4,707,471 | A | 11/1987 | Larm et al. |
| 4,739,046 | A | 4/1988 | DiLuzio et al. |
| 4,761,402 | A | 8/1988 | Williams et al. |
| 4,810,646 | A * | 3/1989 | Jamas et al. .................. 435/101 |
| 4,818,752 | A | 4/1989 | Williams et al. |
| 4,946,450 | A | 8/1990 | Erwin |
| 4,975,421 | A | 12/1990 | Williams et al. |
| 4,992,540 | A | 2/1991 | Jamas et al. |
| 5,028,703 | A * | 7/1991 | Jamas et al. .................. 536/114 |
| 5,032,401 | A | 7/1991 | Jamas et al. |
| 5,037,972 | A | 8/1991 | Jamas et al. |
| 5,057,503 | A | 10/1991 | Czop et al. |
| 5,082,936 | A | 1/1992 | Jamas et al. |
| 5,130,127 | A | 7/1992 | Herlyn |
| 5,221,616 | A | 6/1993 | Kolb et al. |
| 5,223,409 | A | 6/1993 | Ladner et al. |
| 5,223,491 | A | 6/1993 | Donzis |
| 5,250,436 | A | 10/1993 | Jamas et al. |
| 5,320,849 | A | 6/1994 | Hagiwara et al. |
| 5,322,841 | A | 6/1994 | Jamas et al. |
| 5,397,773 | A | 3/1995 | Donzis et al. |
| 5,401,647 | A | 3/1995 | Tanaka et al. |
| 5,453,124 | A | 9/1995 | Moslehi et al. |
| 5,474,984 | A | 12/1995 | Tanaka et al. |
| 5,488,040 | A | 1/1996 | Jamas et al. |
| 5,504,079 | A * | 4/1996 | Jamas et al. .................. 514/54 |
| 5,506,124 | A | 4/1996 | Jamas et al. |
| 5,532,223 | A | 7/1996 | Jamas et al. |
| 5,576,015 | A | 11/1996 | Donzis |
| 5,607,677 | A | 3/1997 | Jamas et al. |
| 5,622,939 | A | 4/1997 | Jamas et al. |
| 5,622,940 | A | 4/1997 | Ostroff |
| 5,633,369 | A | 5/1997 | Jamas et al. |
| 5,663,324 | A | 9/1997 | Jamas et al. |
| 5,702,719 | A | 12/1997 | Donzis |
| 5,705,184 | A | 1/1998 | Donzis et al. |
| 5,741,495 | A | 4/1998 | Jamas et al. |
| 5,766,571 | A | 6/1998 | Ceriani et al. |
| 5,783,569 | A | 7/1998 | Jamas et al. |
| 5,811,542 | A | 9/1998 | Jamas et al. |
| 5,817,643 | A | 10/1998 | Jamas et al. |
| 5,849,720 | A | 12/1998 | Jamas et al. |
| 6,235,272 | B1 | 5/2001 | Greene |
| 6,369,216 | B1 | 4/2002 | Patchen et al. |
| 7,462,607 | B2 | 12/2008 | Cheung |
| 7,507,724 | B2 | 3/2009 | Cheung |
| 7,704,973 | B2 | 4/2010 | Cheung |
| 2004/0014715 | A1 | 1/2004 | Ostroff |
| 2004/0116380 | A1 | 6/2004 | Jamas et al. |

(Continued)

FOREIGN PATENT DOCUMENTS

| CA | 4434938 | 8/2002 |
|---|---|---|
| CN | 1 082 056 A | 2/1994 |

(Continued)

OTHER PUBLICATIONS

Patchen et al., Surv. Immunol. Res., 2: 237-242, 1983.*
Cheung, N-K. V., et al., "Oral (1→3), (1→4)-β-D-Glucan Synergizes with Antiganglioside GD2 Monoclonal Antibody 3F8 in the Therapy of Neurobastoma," *Clinical Cancer Research*, 8: 1217-1223 (May 2002).

(Continued)

*Primary Examiner* — Traviss C McIntosh, III (74) *Attorney, Agent, or Firm* — Hamilton, Brook, Smith & Reynolds, P.C.

(57) ABSTRACT

The invention relates to methods for treating and preventing radiation and/or chemotherapy related injury and/or afflictions, such as myelosuppression and decreased macrophage activity, by administering a prophylactically or therapeutically effective amount of particulate, bioavailable β(1,3; 1,6) glucan. The invention also relates to methods in which β(1,3; 1,6) glucan is provided in the form of whole glucan particles, microparticulate β-glucan particles or a combination thereof.

26 Claims, 2 Drawing Sheets

(56) References Cited

U.S. PATENT DOCUMENTS

| | | | |
|---|---|---|---|
| 2005/0245480 | A1 | 11/2005 | Ostroff et al. |
| 2006/0009419 | A1 | 1/2006 | Ross et al. |
| 2006/0165700 | A1 | 7/2006 | Ostroff et al. |
| 2008/0193456 | A1 | 8/2008 | Cheung |
| 2009/0163439 | A1 | 6/2009 | Ross et al. |
| 2009/0169557 | A1 | 7/2009 | Ross et al. |
| 2010/0216743 | A1 | 8/2010 | Cheung |
| 2010/0273867 | A1 | 10/2010 | Cheung |

FOREIGN PATENT DOCUMENTS

| | | |
|---|---|---|
| CN | 1 694 715 A | 11/2005 |
| CN | 1 697 659 A | 11/2005 |
| CN | 1 939 335 A | 4/2007 |
| CN | 1 964 722 A | 5/2007 |
| EP | 0 416 343 | 3/1991 |
| EP | 1 536 820 | 6/2005 |
| EP | 1 539 194 | 6/2005 |
| EP | 1 545 208 | 6/2005 |
| EP | 1539194 | 6/2005 |
| EP | 2 181 711 | 5/2010 |
| JP | 63-500805 A | 3/1988 |
| JP | 5-502018 A | 4/1993 |
| JP | 11-501691 A | 2/1999 |
| WO | WO 91/03495 A1 | 3/1991 |
| WO | WO 94/03500 A1 | 2/1994 |
| WO | WO 02/058711 A1 | 8/2002 |
| WO | WO 2004/014320 | 2/2004 |
| WO | WO 2004/021994 | 3/2004 |
| WO | WO 2004/021994 A2 | 3/2004 |
| WO | WO 2004/030613 A2 | 4/2004 |
| WO | WO 2006/085895 A2 | 8/2006 |

OTHER PUBLICATIONS

Bohn, J.A., et al., "(1→6)-β-D-Glucans as Biological Response Modifiers: A Review of Structure-Functional Activity Relationships," *Carbohydrate Polymers*, 28: 3-14 (1995).
Yan, J., et al., "β-Glucan, A 'Specific' Biologic Response Modifier That Uses Antibodies to Target Tumors for Cytotoxic Recognition by Leukocyte Complement Receptor Type 3 (CD11b/CD18)," *Journal of Immunology*, 163(6): 3045-3052 (1999).
Wang, S-C., et al., "Targeting HER2: Recent Developments and Future Directions for Breast Cancer Patients," *Seminars in Oncology*, 28(6): 21-29 (2001).
Ross, G.D., et al,, "Therapeutic Intervention with Complement and β-Glucan in Cancer," *Immunopharmacology*, 42(1-3): 61-74 (1999).
Borchers, A.T. et al., "MINIREVIEW: Mushrooms, Tumors, and Immunity," *Proc. Soc. Exp. Biol. Med.*, 221(4): 281-293 (1999).
Patchen, M.L. et al., "Comparative Effects of Soluble and Particulate Glucans on Survival in Irradiated Mice," *J. Biol. Response Mod.*, 5: 45-60 (1986).
Matsuo, T. et al., *Jpn. J Cancer Chemother.*, 14: 1310-1314 (1987). (English Abstract on Last Page).
Turnbull, J.L. et al., "The Polysaccharide PGG-Glucan, Enhances Human Myelopoiesis by Direct Action Independent of and Additive to Early-Acting Cytokines," *Acta. Haematol.*, 102: 66-71 (1999).
Hotta et al., "Augmentation of Protective Immune Responses Against Sendai Virus Infection by Fungal Polysaccharide Schizophyllan," *Int. J. Immunopharmacol.*, 15(1): 55-60 (1993).
Vetvicka, V. et al., "Pilot Study: Orally-Administered Yeast Beta 1,3-Glucan Prophylactically Protects Against Anthrax Infection and Cancer in Mice," *J. Amer. Nutrit. Assoc.*, 5(2): 1-5 (2002).
Nanba et al., "Antitumor Action of Shiitake (Lentinus edodes) Fruit Bodies Orally Administered to Mice," *Chem. Pharm. Bull.* (Tokyo), 35(6): 2453-2458 (1987).
Suzuki et al., "Inhibition of Experimental Pulmonary Metastasis of Lewis Lung Carcinoma by Orally Administered ÿ- Glucan in Mice," *Chem. Pharm. Bull.* (Tokyo), 39: 1606-1608 (1991).
Toi et al., "Randomized Adjuvant Trial to Evaluate the Addition of Tamoxifen and PSK to Chemotherapy in Patients with Primary Breast Cancer," *Cancer*, 70(10): 2475-2483 (1992).

Ross et al., "Specificity of Membrane Complement Receptor Type Three (CR3) for β-Glucans," *Complement. Inflamm.*, 4: 61-74 (1987).
Xia et al., "The ÿ- Glucan-Binding Lectin Site of Mouse CR3 (CD11b/CD18) and Its Function in Generating a Primed State of the Receptor That Mediates Cytotoxic Activation in Response to iC3b-Opsonized Target Cells," *J. Immunol.*, 162: 2281-2290 (1999).
Vetvicka, V. et al., "Soluble ÿ- Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells," *J. Clin. Invest.*, 98(1): 50-61 (1996).
Yan et al., "β- Glucan, a 'Specific' Biologic Response Modifier That Uses Antibodies to Target Tumors for Cytotoxic Recognition by Leukocyte Complement Receptor Type 3 (CD11b/CD18)1," *J Immunol.*, 163: 3045-3052 (1999).
Hassid et al., "The Molecular Constitution of an Insoluble Polysaccharide from Yeast, Saccharomyces cerevisiae," *Journal of the American Chemical Society*, 63: 295-298 (1941).
Database HCAPLUS on STN (Columbus, OH, USA), No. 137:119657, Cheung, N., "Antitumor Antibody-Enhancing Glucan," WO2002058711A1, Aug. 1, 2002, abstract, see entire abstract.
Database DRUGU on STN (Columbus, OH, USA), AN 1998:11655, Coiffier, B., et al, "A Multicenter, Randomized Phase II Study of Rituximab (Chimeric Anti-CD20 mAb) at Two Dosages in Patients with Relapsed or Refractory Intermediate or High-Grade NHL (IHG-NHL) or in Elderly Patients in First-Line Therapy," Blood (90, No. 10, Suppl. 1 Pt 1), 510A, 1997, abstract, see entire abstract.
Database DRUGU on STN (Columbus, OH, USA), AN 1990-03601, Srivastava, R., et al, "Bioactive Polysaccharides from Plants," Phytochemistry, vol. 28, No. 11, pp. 2877-2883, 1989, abstract, see entire abstract.
Sveinbjørnsson, et al., "Macrophage Cytotoxicity Against Murine Meth A Sarcoma Involves Nitric Oxide-Mediated Apoptosis," *Biochem. Biophys. Res. Commun.*, 223(3): 643-649 (1996).
Xia, Y., et al., "The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells," *J. Immunol.*, 162: 2281-2290 (1999).
Thornton, B.P., et al., "Analysis of the Sugar Specificity and Molecular Location of the β-Glucan-Binding Lectin Site of Complement Receptor Type 3 (CD11b/CD18)," *J. Immunol.*, 156: 1235-1246 (1996).
Ross, G.D., et al., "Membrane Complement Receptor Type Three (CR3) has Lectin-Like Properties Analogous to Bovine Conglutinin and Functions as a Receptor for Zymosan and Rabbit Erythrocytes as well as a Receptor for iC3b," The Journal of Immunology, 134(5): 3307-3315 (1985).
Ross, G.D., et al, "Specificity of Membrane Complement Receptor Type Three (CR3) for β-Glucans," *Complement*, 4: 61-74 (1987).
Cain, J.A., et al, "Role of Complement Receptor Type Three and Serum Opsonins in the Neutrophil Response to Yeast," *Complement*, 4: 75-86 (1987).
Suzuki, I., et al, "Inhibition of Experimental Pulmonary Metastais of Lewis Carcinoma by Orally Administered β-Glucan in Mice," *Chem. Pharm. Bull.*, 39(6): 1606-1608 (1991).
Roubey, et al, "Staurosporine Inhibits Neutrophil Phatocytosis but not iC3b Binding Mediated by CR3 (CD11b/CD18)," *The Journal of Immunology*, 146(10): 3557-3562 (1991).
Ross, G.D., et al., "CR3 (CD11b, CD18): A Phagocyte and NK Cell Membrane Receptor with Multiple Ligand Specificities and Functions," *Clin Exp Immunol*, 92: 181-184 (1993).
Muto, Satoshi, et al., "CR3 (CD11b/CD18) Expressed by Cytotoxic T Cells and Natural Killer Cells is Upregulated in a Manner Similar to Neutrophil CR3 Following Stimulation with Various Activating Agents," Journal of Clinical Immunology, 13(3): 175-184 (1993).
Vetvicka, V., et al., "Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells," *J. Clin. Invest.*, 98(1): 50-61 (1996).

(56) References Cited

OTHER PUBLICATIONS

Vetvicka, V., el al., "Targeting of Natural Killer Cells to Mammary Carcinoma via Naturally Occurring Tumor Cell-Bound iC3b and beta-glucan-primed CR3 (CD11b/CD18)," *J. Immunol*, 159(2): 599-605 (1997).
Reddy, R.K., el al., "A Mixed Population of Immature and Mature Leucocytes in Umbilical Cord Blood Results in a Reduced Expression and Function of CR3 (CD11b/CD18)," *Clin Exp Immunol*, 114: 462-467 (1998).
Xia, Y., et al., "Generation of Recombinant Fragments of CD11b Expressing the Functional β-Glucan-Binding Lectin Site of CR3 (CD11b/CD18)," *The Journal of Immunology*, 162(12): 7285-7293 (1999).
Vetvicka, V., et al., "Regulation of CR3 (CD11b/CD18)-dependent Natural Killer (NK) Cell Cytotoxicity by Tumour Target Cell MHC Class I Molecules," *Clin Exp Immunol*, 115: 229-235 (1999).
Yan, J., et al., "Critical Role of Kupffer Cell CR3 (CD11b/CD18) in the Clearance of IgM-Opsonized Erythrocytes or Soluble β-Glucan," *Immunopharmacology*, 46: 39-54 (2000).
Ross, G.D., "Regulation of the Adhesion Versus Cytotoxic Functions of the Mac-1/CR3/$\beta_m\beta_2$ Integrin Glycoprotein," *Critical Reviews in Immunology*, 20:197-222 (2000).
Ross, G.D., "Role of the Lectin Domain of Mac-1/CR3 (CD11b/CD18) in Regulating Intercellular Adhesion," *Immunologic Research*, 25(3): 219-227 (2002).
Biopolymer Engineering Presentation: Pioneering Carbohydrate Technology to Improve Human Health, Apr. 2003.
Blakeslee, Dennis, "The Two Faces of Immunity: Th1 and Th2," JAMA HIV/AIDS Resource Center, The Journal of the American Medical Association, (Aug. 12, 2002).
"What's the Difference of Th1 Cells and Th2 Cells Effect?" (May 8, 1999).
Heron Herbals: Feature Articles: "Balancing Cellular and Humoral Immunity," (Aug. 16, 2002).
Kournikakis et al., "Anthrax-Protective Effects of Yeast Beta 1,3 Glucans," Medscape General Medicine, Mar. 21, 2003, 4 sheets.
Bögwald et al., "The Cytotoxic Effect of Mouse Macrophages Stimulated in vitro by a beta-1,3,-D-Glucan from yeast Cell Walls," *Scand. J. Immunol.*, 15: 297-304 (1982).
Czop et al., "Production and isolation of rabbit anti-idiotypic antibodies directed against the . . . ," *J Immunol*, 145: 995-1001 (1990).
Czop et al., "The Role of β-Glucan Receptors on Blood and Tissue Leukocytes in Phagocytosis and Metabolic Activation," *Pathology and Immunopathology Research*, 5: 286-296 (1986).
Leyland-Jones, B., "Trastuzumab: Hopes and Realities," *The Lancet ONCOLOGY*, vol. 3: 137-144 (Mar. 2002).
Bystryn, J-C., "Tumor Vaccines," *Cancer and Metastasis Reviews*, 9: 81-91 (1990).
Gura, T., "Systems for Identifying New Drugs Are Often Faulty," *Science*, 278: 1041-1042 (1997).
"Principles of Cancer Therapy," Cecil's Textbook of Medicine (21st Edition, vol. 1), W.B. Saunders Company, Goldman, L., ed., pp. 1060-1074 (2000).
Chihara, et al., "Fractionation and Purification of the Polysaccharides with Marked Antitumor Activity, Especially Lentinan, from Lentinus edodes (Berk.) Sing. (an Edible mushroom)," Cancer Research, 30: 2776-2781 (1970).
Coxon, A. et al., "A Novel Role for the Beta2 Integrin CD11b/CD18 in Neutrophil Apoptosis: A Homeostatic Mechanism in Inflammation," *Immunity*, 5: 653-666 (1996).
Database Medline in STN. (Columbus, OH, USA) AN 2000285552, Yadomae, T., "Structure and Biological Activities of Fungal beta-1,3-glucans," *J. Pharmaceutical Soc. Jap.*, 120(5): 413-431 (2000), Abstract Only.
Diller, et al., "The effect of yeast polysaccharides on mouse tumors," Institute for Cancer Research, vol. 23 (Feb. 1963).
Gelderman, et al., "Complement function in mAb-mediated cancer immunotherapy," Trends in Immunol. 25:158-164, 2004).
Harlow, E. and Lane, D., "Using antibodies: a laboratory manual," (NY: Cold Spring Harbor Laboratory Press) (1999).
Hassid, et al., "The Molecular Constitution of an Insoluble Polysaccharide from Yeast, *Saccharomyces cerevisiae*," Journal of the American Chemical Society, 63: 295 (1941).
Hortobagyi, "Overview of treatment results with trastuzumab (Herceptin) in metastatic breast cancer," Semin Oncol. 28:43-47 (2001) Abstract Only.
Hotta et al., "Augmentation of Protective Immune Responses Against Sendai Virus Infection by Fungal Polysaccharide Schizophyllan," *Int. J. Immunopharmarmacol.*, 15(1): 55-60 (1993).
Kaiser, A.B. et al., "Synergism Between Poly-(1-6)-Beta-D-Glucopyranosyl-(1,3)-Beta-D-Glucopyranose Glucan and Cefazolin in Prophylaxis of *Staphylococcal* Wound Infection in a Guinea Pig Model," *Antimicrob. Agents Chemother.*, 42(9): 2449-2451 (1998).
Li, B., et al., "Combined Yeast β-Glucan and Antitumor Monoclonal Antibody Therapy Requires C5a-Mediated Neutrophil Chemotaxis via Regulation of Decay-Accelerating Factor CD55," *Cancer Research*, 67(15): 7421-7430 (2007).
Li, B., et al., "Yeast β-Glucan Amplifies Phagocyte Killing of iC3b-Opsonized Tumor Cells via Complement Receptor 3-Syk-Phosphatidylinositol 3-Kinase Pathways[1]," *The Journal of Immunology*,177: 1661-1669 (2006).
Maeda, et al., "Denaturation and Renaturation of a β-1,6;1,3-Glucan, Lentinan, Associated with Expression of T-Cell-mediated Responses," Cancer Research, 48: 671-675 (1988).
Matsuo, T. et al., "Granulopoietic Effects of Lentinan in Mice: Effects on GM-CFC and 5-FU-Induced Leukopenia," *Jpn. J. Cancer Chemotherapy*, 14: 1310-1314 (1987) (English Abstract on Last Page).
Nanba et al., "Antitumor Action of Shiitake (Lentinus edodes) Fruit Bodies Orally Administered to Mice," *Chem. Pharm. Bull*, (Tokyo), 35(6): 2453-2458 (1987).
Onderdonk, A. et al., "Anti-Infective Effect of Poly-Beta 1-6-Glucotriosyl-Beta 1-3-Glucopyranose Glucan in vivo," *Infect. Immun.*, 60(4): 1642-1647 (1992).
Patchen, M.L. et al., "In vitro and in vivo Hematopoietic Activities of Betafectin® PGG-Glucan," *Exp. Hematol.*, 26: 1247-1254 (1998).
Patchen, M.L., "Immunomodulators and Hemopoiesis," *Surv. Immunol. Res.*, 2: 237-242 (1983).
Ross, G.D. et al., "Newly Identified Function for the Complement (C) System in Regulating Hematopoiesis and Bone Marrow Reconstitution After Radiation Injury," *Experimental Hematology*, 31(7, Suppl. 1): 235-236 (2003).
Toi, et al., "Randomized Adjuvant Trial to Evaluate the Addition of Tamoxifen and PSK to Chemotherapy in Patients with Primary Breast Cancer," *Cancer*, 70(10): 2475-2483 (1992).
Turnbull, J.L. et al., "The Polysaccharide PGG-Glucan, Enhances Human Myelopoiesis by Direct Action Independent of an Additive to Early-Acting Cytokines," *Acta. Haemato1.*, 102: 66-71 (1999).
Vetvicka, V. et al., "Pilot Study: Orally Administered Yeast Beta 1,3-Glucan Prophylactically Protects Against Anthrax Infection and Cancer in Mice," *J. Amer. Nutrit. Assoc.*, 5(2):1-5 (2002).
Wessels, M.R. et al., "Studies of Group B Stretococcal Infection in Mice Deficient in Complement Component C3 or C4 Demonstrate an Essential Role for Complement in Both Innate and Acquired Immunity," *Proc. Natl. Acad. Sci. USA*, 92: 11490-11494 (1995).
www.breastcancer.org (Accessed online at http://www.breastcancer.org/tips/immune/helping.jsp) Mar. 31, 2009.
www.cancerbackup.org (Accessed online at http://www.cancerbackup.org.uk/QAs/BiologicaltherapiesQAs/Monoclonalantibodies/related_faqs QAs/521) Mar. 31, 2009.
Suzuki et al., "Biological Activities of Polysaccharides," Gann, 1969, vol. 60, No. 3, pp. 273-277—Abstract only provided.
Patchen, M.L. et al., "Comparative Effects of Soluble and Particulate Glucans on Survival in Irradiated Mice," *Journal of Biological Response Modifiers*, 5(1): 45-60 (1986).
Patchen, M.L. et al., "Glucan: Mechanisms Involved in its 'Radioprotective' Effect," *Journal of Leukocyte Biology*, 42: 95-105 (1987).
Pedroso, M., "Application of Beta-1,3-Glucan to Prevent Shipping Fever in Imported Heifers," *Archives of Medical Research*, 25(2): 181 (1994).

(56) References Cited

OTHER PUBLICATIONS

Patchen, M.L. et al., "Soluble Polyglycans Enhance Recovery from Cobalt-60-Induced Hemopoietic Injury," *Journal of Biological Response Modifiers*, 3: 627-633 (1984).

Patchen, M.L. et al., "Effects of Pre- and Post-Irradiation Glucan Treatment on Pluripotent Stem Cells, Granulocyte, Macrophage and Erythroid Progenitor Cells, and Hemopoietic Stromal Cells," *Experientia*, 40: 1240-1244 (1984).

Petruczenko, A., "Glucan Effect on the Survival of Mice After Radiation Exposure," *Acta. Physiol. Pol.*, 35(3): 231-236 (1984).

Patchen, M.L. et al., "Stimulated Hemopoiesis and Enhanced Survival Following Glucan Treatment in Sublethally and Lethally Irradiated Mice," *Int. Journal of Immunopharmacology*, 7(6): 923-932 (1985).

Patchen, M.L. et al., "Glucan-Induced Hemopoietic and Immune Stimulation: Therapeutic Effects in Sublethally and Lethally Irradiated Mice," *Methods Find. Exp. Clin. Pharmacol.*, 8(3): 151-155 (1986).

Wagnerova, J. et al., "The Effect of Two Glucan Carboxymethyl Derivatives with Various Substitution Degrees on Cyclophosphamide Immunosuppression in Mice," *Immunopharmacol.and Immunotoxicol.*, 15(2&3): 227-242 (1993).

International Search Report for Int'l Application No. PCT/US03/27841; Date Mailed: Jun. 21, 2004.

International Preliminary Examination Report for Int'l Application No. PCT/US03/27841; Date Mailed: Dec. 6, 2004.

Supplementary European Search Report for European Application No. EP 03 74 9452; Date Mailed: Apr. 16, 2007.

European Search Report for European Application No. EP 10 00 1786; Date Mailed: Mar. 16, 2010.

Misaki, A., "Structure of Pestalotan, A Highly Branched (1→3)-β-D-Glucan Elaborated by *Pestalotia sp.* 815, and the Enhancement of its Antitumor Activity by Polyol Modification of the Side Chains," *Carbohydr. Res.*, 129: 209-227 (Jan. 1984).

International Search Report for Int'l Application No. PCT/US2003/025237; Date Mailed: Jul. 9, 2004.

International Preliminary Examination Report for Int'l Application No. PCT/US2003/025237; Date Mailed: Jun. 24, 2005.

Supplementary European Search Report for European Application No. EP 03 78 5229; Date Mailed: Feb. 9, 2006.

International Search Report for Int'l Application No. PCT/US2005/016229; Date Mailed: Jul. 27, 2006.

Written Opinion for Int'l Application No. PCT/US2005/016229; Date Mailed: Jul. 27, 2006.

International Preliminary Examination Report for Int'l Application No. PCT/US2005/016229; Date Mailed: Nov. 14, 2006.

International Search Report for Int'l Application No. PCT/US03/27975; Date Mailed: May 24, 2004.

International Preliminary Examination Report for Int'l Application No. PCT/US03/27975; Date Mailed: Dec. 15, 2004.

Supplementary European Search Report for European Application No. EP 03 78 6508; Date Mailed: May 11, 2007.

Graziero, L. et al., "Adoptive Immunotherapy Prevents Prostate Cancer in a Transgenic Animal Model," *Eur. J. Immunol.*, 29: 1127-1138 (1999).

Byers, T., "What Can Randomized Controlled Trials Tell Us About Nutrition and Cancer Prevention?" *CA-A Cancer Journal for Clinicians*, 49(6): 353-361 (Nov./Dec. 1999).

Frazer, I., "Is Vaccine Therapy the Future in Cancer Prevention?" *Expert. Opin. Pharmacother.*, 5: 2427-2434 (2004).

Notice of Opposition of European Patent No. 1536820 dated Feb. 8, 2011.

Encyclopedia article titled "Lentinan", obtained from http://en.wikipedia.org/wiki/Lentinan on Dec. 10, 2010, last updated Nov. 30, 2010 as shown by chronological record of updates to the article which is included as part of the article.

News Release from Biothera titled "DKSH to Distribute Biopolymer Engineering Beta 1,3/1,6 Glucan in Europe", published Dec. 16, 2003, obtained on Dec. 9, 2010 from http:www.biothera.com/press/12-16-03%20DKSH.htm.

Chen et al., Abstract from "Medicinal Importance of fungal β-(1→3),(1→6)-glucans", Mycological Research III, (2007) p. 635-652.

Hamuro et al., "Solid phase activation of alternative pathway of complement by beta-1,3-glucans and its possible role for tumour regressing activity", *Immunology*, 34(4):695-705 (1978).

Communication Pursuant to Article 94(3) EPC for European Application No. EP 03 78 6508; Date Mailed: Mar. 3, 2011.

\* cited by examiner

METHODS OF USING BETA GLUCAN AS A RADIOPROTECTIVE AGENT

RELATED APPLICATIONS

This application is a continuation of U.S. application Ser. No. 11/057,102, filed Feb. 11, 2005, which is a continuation of International Application No. PCT/US03/25237, which designated the United States and was filed on Aug. 13, 2003, published in English, which claims the benefit of U.S. Provisional Application No. 60/403,424, filed on Aug. 13, 2002. The entire teachings of the above applications are incorporated herein by reference.

GOVERNMENT SUPPORT

The invention was supported, in whole or in part, by grant CA84612 from the National Institutes of Health and by grant DAMD17-02-1-0445 from the U.S. Army. The Government has certain rights in the invention.

BACKGROUND OF THE INVENTION

Beta(β)-glucan is a complex carbohydrate, generally derived from several sources, including yeast, bacteria, fungi and cereal grains. Each type of β-glucan has a unique structure in which glucose is linked together in different ways, resulting in different physical and chemical properties. For example, β(1,3) glucan derived from bacterial and algae is linear, making it useful as a food thickener. The frequency of side chains, known as the degree of substitution or branching frequency, regulated secondary structure and solubility. Beta glucan derived from Yeast is branched with β(1,3) and β(1,6) linkages, enhancing its ability to bind to and stimulate macrophages. β(1,3/1,6) glucan purified from baker's yeast (*Saccharomyces cerevisiae*) is a potent anti-infective beta-glucan immunomodulator.

The cell wall of *S. cerevisiae* is mainly composed of β-glucans, which are responsible for its shape and mechanical strength. While best known for its use as a food grade organism, yeast is also used as a source of zymosan, a crude insoluble extract used to stimulate a non-specific immune response. Yeast-derived beta(1,3) glucans stimulate the immune system, in part, by activating the innate anti-fungal immune mechanisms to fight a variety of targets. Baker's yeast β(1,3/1,6) glucan is a polysaccharide composed entirely of β(1,3)-linked sugar (glucose) molecules forming the polysaccharide backbone with periodic β(1,3) branches linked via β(1,6) linkages). It is more formally known as poly-(1,6)-β-D-glucopyranosyl-(1,3)-β-D-glucopyranose. Glucans are structurally and functionally different depending on the source and isolation methods.

Beta glucans possess a diverse range of activities. The ability of β-glucan to increase nonspecific immunity and resistance to infection is similar to that of endotoxin. Early studies on the effects of β(1,3) glucan on the immune system focused on mice. Subsequent studies demonstrated that β(1,3) glucan has strong immunostimulating activity in a wide variety of other species, including earthworms, shrimp, fish, chicken, rats, rabbits, guinea pigs, sheep, pigs cattle and humans. Based on these studies, β(1,3) glucan represents a type of immunostimulant that is active across the evolutionary spectrum, likely representing an evolutionarily innate immune response directed against fungal pathogens. However, despite extensive investigation, no consensus has been achieved on the source, size, and form of β(1,3) glucan ideal for use as an immunostimulant.

Radiation and chemotherapeutic drugs can suppress the production of blood cells and platelets in the bone marrow, an adverse side-effect known as myelosuppression. Exposure to radiation can cause a rapid depletion of immune (hematopoietic) cells and platelets derived from the bone marrow (BM) that are necessary for controlling life threatening infections and bleeding episodes.

Radioprotectants allow for more effective antitumor treatments by minimizing the side effects of radiotherapy or chemotherapy. Advances in radioprotection also enable military forces to operate, when required, in nuclear or radioactive combat environments while minimizing both long-term and short-term risks of the consequences of exposure to ionizing radiation. Radioprotectants can also be useful for protecting or treating astronauts who are exposed to space radiation. Finally, readily available and easily administered radioprotectants could be of crucial importance in minimizing the damage from terrorist actions or industrial nuclear accidents.

The use of β(1,3/1,6) glucans as hematopoietic agents has been tentatively explored in several references. For example, U.S. Pat. No. 5,532,223 by Jamas et al. demonstrates the use of parenteral neutral soluble glucan to stimulate hematopoietic and immunological effects without stimulating the production of undesired cytokines. Patchen and colleagues demonstrated that parenterally administered soluble and particulate beta-glucans can enhance hematopoietic recovery and the ability to resist infection in mice exposed to radiation when administered either before or after exposure to radiation. See M. L. Patchen et al., "Glucan: mechanisms involved in its 'radioprotective' effect", *J. Leukoc. Biol.*, 42, 95 (1987). Beta glucan has also been used as a topical antioxidant to protect the skin from damage caused by ultraviolet radiation. See J. A. Greene, "Composition for protecting skin from damaging effects of ultraviolet light", U.S. Pat. No. 6,235,272. However, these laboratory studies have not provided a convenient formulation of β-glucan. The majority of these applications utilize soluble material that requires administration by injection, a costly and painful route that can result in poor patient compliance. However, many drugs are not amenable to oral formulation due to properties that limit oral bioavailability. Therefore, a need exists for formulations that can lead to greater patient compliance and maintain bioavailability. Additionally, there remains a need for a formulation of β-glucan, particularly an oral formulation, which can be readily stored and administered to humans to prevent or treat myelosuppression and serve as an effective radioprotectant.

SUMMARY OF THE INVENTION

The present invention relates to the use of particulate, bioavailable, β(1,3/1,6) glucan as a radioprotectant. The β(1,3/1,6) glucan can be readily administered orally and is bioavailable to the site of action (e.g., bone marrow). Disclosed herein is a method of treating and preventing injury from ionizing radiation and/or chemotherapy by administering a prophylactically or therapeutically effective amount of particulate, bioavailable β(1,3/1,6) glucan. In a certain embodiments, the β(1,3/1,6) glucan comprises whole glucan particles, microparticulate β-glucan particles or a combination of whole glucan particles and microparticulate β-glucan particles. Whole glucan particles typically have a diameter of 1 micron or greater and microparticulate β-glucan particles a diameter of 1 micron or less. The whole glucan particles, microparticulate β-glucan particles or a combination of whole glucan particles and microparticulate β-glucan particles may be administered orally and/or parenterally, with oral administration of whole glucan particles being preferred.

Ranges of about 0-100 mg/kg of body weight of body weight of β-glucan administered daily constitute a therapeutically effective dose.

The present invention also discloses a method of treating and preventing radiation and/or chemotherapy related afflictions, such as myelosuppression and decreased macrophage activity by administering a prophylactically or therapeutically effective amount of β(1,3/1,6) glucan. The radiation and/or chemotherapy related afflictions may be caused either by ionizing radiation, chemotherapy, or other adverse conditions. Oral administration of a daily therapeutically effective dose of about 0-100 mg/kg of body weight of whole glucan particles is particularly preferred. The glucan can be co-administered with other agents for enhancing stem cell activation.

The invention also relates to methods of treating or preventing the reduction of macrophage activity created by radiation or chemotherapy by administering a prophylactically or therapeutically effective amount of particulate, bioavailable β(1,3/1,6) glucan. In another embodiment, the invention relates to the use of a particulate bioavailable β(1,3/1,6) glucan for the manufacture of a medicament for oral use in treating myelosuppression following radiation, wherein the orally administered glucan enhances hematopoietic stem progenitor cells by functioning with the complement system by providing a second signal for CR3 activation.

Also described herein are methods of enhancing glucan-mediated hematopoietic progenitor stem cell recovery after exposure to radiation via the complement system, comprising administering to an individual a therapeutically effective orally bioavailable amount of whole glucan particles, wherein the glucan enhances regeneration of hematopoietic progenitor stem cells. The β(1,3/1,6) glucan functions with complement activation after injury to promote stem cell attachment to the injury site via stem cell CR3 binding to iC3b stem cells that are attached via iC3b by providing the "second signal" for CR3 activation. This ligation of glucan to the lectin domain of CR3 is more efficient than the natural lectin site signal mediated by damaged tissue heparin sulphate. In certain embodiments of the methods of the invention, the orally administered glucan is transported to the bone marrow and degraded. At the bone marrow, the degraded oral glucan activates stem cells via the complement system by binding to iC3b deposited on injured stem cell and activating CR3. That is, the method of the invention pertains to a method of enhancing glucan-mediated hematopoietic progenitor stem cell recovery after exposure to radiation via the complement system, comprising administering to an individual a therapeutically effective orally bioavailable amount of whole glucan particles, wherein the glucan via the complement system enhances regeneration of hematopoietic progenitor stem cells. The orally administered glucan is taken up by macrophages, transported to the bone marrow, degraded and the released fragments primes the CR3 of stem cell thereby activating the stems cell to differentiate and proliferate. The β(1,3/1,6) glucan in via the complement system promotes stem cell proliferation and differentiation by binding to iC3b deposited on injured stem cells and activating CR3.

DETAILED DESCRIPTION OF THE PREFERRED EMBODIMENTS

The present invention relates to methods of using an oral, bioavailable β(1,3/1,6) glucan as a pharmaceutical agent for the treatment and prevention of radiation and/or chemotherapy related injuries and/or afflictions, such as myelosuppression and decreased macrophage activity. Moreover, the present invention relates to methods of using β(1,3/1,6) glucan in whole glucan particle form and/or microparticulate β-glucan particle form as an agent, such as a pharmaceutical or dietary, for the treatment and prevention of radiation and/or chemotherapy related afflictions. Additionally, the present invention relates to the use of β(1,3/1,6) glucan in whole glucan particle form, microparticulate β-glucan particle form or any combination thereof as a radioprotectant.

Whole glucan particle (WGP) is a purified, yeast cell wall preparation. The whole glucan particles are produced by removing the mannan protein outer layer and exposing the β-glucan while retaining glucan's in vivo morphology. In certain embodiments, the whole glucan particles have a particle size of 1 micron or greater. Microparticulate glucan particles are defined herein to be portions of whole glucan particles that result from finely grinding yeast cell wall β(1,3/1,6) glucan down to a particle size of about 1 micron or less. The preparation and use of these compounds for the prevention and treatment of myelosuppression is described below.

Various forms of particulate and soluble β-glucans have been prepared. One example is microparticulate glucan particles, which can be formed by finely grinding yeast cell wall β(1,3/1,6) glucan down to a particle size of about 1 micron or less. Beta glucan in this form has been applied to use as a nutritional supplement and skin restorer, such as disclosed in U.S. Pat. No. 5,702,719, by Donzis. Other useful particulate glucan useful in the methods described herein, are WGP™ Beta Glucan and BetaRight™ obtained from Biopolymer Engineering, Inc., Eaton, Minn.

Microparticulate β-glucan particles have also been shown to enhance the host's immune system. See U.S. Pat. Nos. 5,223,491 and 5,576,015, the teachings of which are incorporated herein by reference in their entirety. Another form is neutral soluble β-glucans, which are prepared through a series of acid, alkaline, and neutral treatment steps to yield a conformationally pure neutral soluble glucan preparation. The neutral soluble glucan preparation enhances a host's immune system but does not induce the production of IL-1 and TNF and thus do not cause inflammation. See U.S. Pat. No. 5,783,569, the teachings of which are incorporated herein by reference in its entirety.

Another form of β-glucan is an insoluble particle known as whole glucan particles (WGP). Whole glucan particles are the remnants of the yeast cell wall prepared by separating growing yeast from its growth medium and subjecting the intact cell walls of the yeast to alkali, thus removing unwanted proteins and nucleic acid material. In certain embodiments, what remains is a spherical beta-glucan particle with the outer mannan protein removed. Whole glucan particles may be obtained from any glucan-containing fungal cell wall source, but the preferred source is a strain of *S. cerevisiae*. These insoluble particles have been shown to enhance host resistance to a wide range of infections, increase antibody production (adjuvant activity), increase leukocyte mobilization, and enhance wound healing. Methods of producing WGP are known in the art and are disclosed in U.S. Pat. Nos. 4,810,646, 4,492,540, 5,037,972, 5,082,936, 5,250,436, and 5,506,124, the contents of which are incorporated herein by reference in their entirety. WGP can be further broken down into various components, each with differing affinities for binding to subsets of receptors found on innate immune cells. These various conformational forms are, in increasing order of complexity, random coil, single helix, triple helix, and triple helical multimer. WGP has shown a variety of biological activities, including use as a vaccine adjuvant (U.S. Pat. No. 5,741,495), an anti-infective agent (Pedroso M., "Application of beta-1, 3-glucan to prevent shipping fever in imported heifers," *Arch. Med. Res.* 25(2), 181 (1994)), and an antitumor agent (Borchers, A. T., et al., *Proc. Soc. Exp. Biol. Med.*, 221(4), 281 (1999)). Each conformational form possesses different activities as is demonstrated by the different specificities observed for glucan receptors.

The β-glucans for use in the methods described herein are oral bioavailable formulations. Bioavailable as used herein means the whole glucan particle is able to reach the target of action, The whole glucan particle has enough β(1,3/1,6) glucan exposed for peyer's patch uptake of the glucan. The glucan is taken up in the Peyer's patch and engulfed and degraded by macrophages, transported to the bone marrow where the degraded fragments are released. The degraded fragments activate the complement system by binding to iC3b deposited on injured stem cell and activate CR3. For example, the WGP is able to reach and act on the bone marrow or other stem cell. At the site of action, the glucan acts to stimulate stem cells as a result of the binding or association of the glucan to the CR3 receptor that in turn primes or promotes the CR3 for action. The bioavailability of oral WGP is mediated by the transport of WGP to the bone marrow by gastrointestinal macrophages that degrade the particle. The degraded particles then function at the bone marrow as stimulators of stem cell CR3 activation.

Mylosuppression

One of the deleterious effects of gamma radiation exposure is damage to the bone marrow depleting the body of white blood cells that defend against infection and disease. β-glucans have the ability to stimulate hematopoiesis in an analogous manner as granulocyte monocyte-colony stimulating factor (GM-CSF). Radiation and chemotherapy suppress blood cell production because blood cells are constantly proliferating to replace old blood cells, and proliferating cells are more susceptible to damage. If blood cell counts become too low, chemotherapy may have to be reduced or postponed, and patients may require transfusions of red blood cells (RBC's), white blood cells (WBC's), or platelets until the bone marrow begins to function adequately. Red blood cells are required to carry oxygen to the cells of the body, and exist in a normal range of 3,800-5,400, which is determined by the hemoglobin and hematocrit. A decrease in either or both the hemoglobin and hematocrit may lead to anemia. Platelets play an important role in blood clotting. Normally, platelet number ranges from 150,000-400,000. Lower than normal counts will tend to cause excessive bleeding, exemplified by bleeding gums, nosebleeds, and severe bruising. White blood cells are crucial for fighting infection. Their normal range is 4,500-11,000, and lower counts increase your susceptibility to infection. Adequate immune resistance is lost if WBC counts fall below 1,500-2,000.

One cause of myelosuppression is exposure to radioactive materials, either intentionally as part of radiotherapy, or accidentally due to terrorism, military use, or a nuclear spill. Radioactive materials decay spontaneously to produce ionizing radiation, which has sufficient energy to damage living tissue. The various forms of ionizing radiation are alpha and beta particles, and gamma or X-rays. The energy of these various particles and rays determines the extent of penetration into tissue, and the extent of damage. The type and severity of injuries produced by radiation depends on the dose, dose rate, radiation quality, and type of exposure (whole body vs. local). In mice, death following whole-body irradiation in the 700-1,000 rad dose range usually occurs 10 days or longer after exposure, and results from irreversible bone marrow damage. Lower doses or radiation may result in non-fatal erythrocytopenia, lymphocytopenia, and granulocytopenia, a condition known as myelosuppression. Medical patients receiving radiation treatments often exhibit myelosuppression because they are receiving relatively high "bursts" of radiation during treatment.

β-Glucan, a well-known biological response modifier (BRM), stimulates hematopoiesis (blood cell formation), in an analogous manner as granulocyte monocyte-colony stimulating factor (GM-CSF). Research was carried out initially with particulate β-glucan and later with soluble β-glucans, all of which were administered intravenously to mice (Patchen M. L., et al., *J. Biol. Response Mod.* 3:627-633 (1984), Patchen, M. L., et al., *Experientia* 40:1240-1244 (1984), Petruczenko, A. *Acta. Physiol. Pol.* 35:231-236 (1984) and Patchen, M. L. and T. J. MacVittie., *Int. J. Immunopharmacol.* 7:923-932 (1985)). Mice exposed to 500-900 cGy of gamma radiation exhibited a significantly enhanced recovery of blood leukocyte, platelet and red blood cell counts when given i.v. β-glucans (Patchen, M. L. and T. J. MacVittie. *J. Biol. Response Mod.* 5:45-60 1986) and Patchen, M. L., et al., *Methods Find. Exp. Clin. Pharmacol.* 8:151-155 (1986)). Other reports showed that β-glucan could reverse the myelosuppression produced with chemotherapeutic drugs such as fluorouracil (Matsuo, T., et al., *Jpn. J. Cancer Chemother.* 14:1310-1314 (1987) or cyclophosphamide (Wagnerová, J., et al., *Immunopharmacol. Immunotoxicol.* 15:227-242 (1993) and Patchen, M. L et al., *Exp. Hematol.* 26:1247-1254 (1998)). Moreover, the anti-infective activity of β-glucan combined with its hematopoiesis-stimulating activity resulted in enhanced survival of mice receiving a lethal dose of 900-1200 cGy of radiation. In vitro studies showed that β-glucan could enhance granulocyte and megakaryocyte colony formation by hematopoietic stem progenitor cells when used in combination with GM-CSF and interleukin-3 (IL-3), respectively (Turnbull, J. L et al., *Acta Haematol.* 102:66-71 (1999)). Development of β-glucans for their hematopoietic activity was not considered worthwhile at that time because of advent of GM-CSF as a therapeutic agent. The Armed Forces Radiobiological Research Institute (AFRRI) that did much of the early research showing the radioprotective effects of β-glucan also considered β-glucan use to protect individuals exposed to radiation as a result of a nuclear power plant accident or nuclear war. However, the apparent need to administer β-glucans intravenously made it unfeasible to rapidly treat large numbers of people in such emergency situations.

Subsequently, as described herein, the oral immunomodulatory activities of β-glucans have been recognized. It is believed that the oral uptake of certain β-glucans by M (microfold) cells in intestinal Peyer's patches leads to β-glucan presentation to macrophages in the underlying gut-associated lymphatic tissue (GALT). Orally delivered mushroom β-glucans have been shown to activate peritoneal and alveolar macrophages. Further, oral administration of the shiake mushroom-derived β-glucan, lentinan has been found to increase the number of T helper cells in blood of rats. Oral β-glucan has also been shown to induce anti-infective (Hotta, H., K. et al., *Int. J. Immunopharmacol.* 15:55-60 (1993) and Vetvicka, V., K. *J. Amer. Nutrit. Assoc.* 5:1-5 (2002)) and anti-tumor activities in both preclinical and clinical studies (Nanba, H., K. et al., *Chem. Pharm. Bull.* (*Tokyo*) 35:2453-2458 (1987); Suzuki, I., T. et al., *Chem. Pharm. Bull.* (*Tokyo*) 39:1606-1608 (1991) and Toi, M., T. et al., *Cancer* 70:2475-2483 (1992)). Summarizing available data, β-glucans function by stimulating host immune defense mechanisms, primarily macrophages, neutrophils, NK cells, and dendritic cells, thereby enhancing microbial or tumor cell clearance and subsequently reducing mortality (Onderdonk, A., et al., *Infect. Immun.* 60:1642-1647 (1992) and Kaiser, A. B. and D. S. Kernodle., *Antimicrob. Agents Chemother.* 42:2449-2451 (1998)).

Yeast-derived β(1,3/1,6) glucans work, in part, by stimulating innate anti-fungal immune mechanisms to fight a range of pathogenic challenges from bacteria, fungi, parasites, viruses, and cancer. Research to define the mechanism of action of β-glucans has shown that they function through the priming of macrophages, neutrophils, monocytes, and NK cells, giving these cells an enhanced activity to kill microbial pathogens or tumor cells. Beta glucans from various sources with different structures have been shown to bind to a variety of receptors. Mannans, galactans, α(1,4)-linked glucose polymers and β(1,4)-linked glucose polymers have no avidity for the receptor located on the cells. Two β-glucan-binding receptors on leukocytes have been characterized that function to promote the phagocytosis of yeast cells walls via binding to β-glucan. First, the iC3b-receptor CR3 (also known as Mac-1, CD11b/CD18, or $\alpha_M\beta_2$-integrin) was shown to have a β-glucan-binding lectin site that functioned in the phagocytosis of yeast cell walls by neutrophils, monocytes, and macrophages (Ross, G. D., et al., *Complement Inflamm.* 4:61-74 (1987) and Xia, Y., V. et al., *J. Immunol.* 162:2281-2290 (1999)). Mac-1/CR3 functions as both an adhesion molecule mediating the diapedesis of leukocytes across the endothelium and a receptor for the iC3b fragment of complement responsible for phagocytic/degranulation responses to microorganisms. Mac-1/CR3 has many functional characteristics shared with other integrins, including bidirectional signaling via conformational changes that originate in either the cytoplasmic domain or extracellular region. Another key to its functions is its ability to form membrane complexes with glycosylphosphatidylinositol (GPI)-anchored receptors such as Fc gammaRIIIB (CD16b) or uPAR CD87), providing a transmembrane signaling mechanism for these outer membrane bound receptors that allows them to mediate cytoskeleton-dependent adhesion or phagocytosis and degranulation. Many functions appear to depend upon a membrane-proximal lectin site responsible for recognition of either microbial surface polysaccharides or GPI-linked signaling partners. Because of the importance of Mac-1/CR3 in promoting neutrophil inflammatory responses, therapeutic strategies to antagonize its functions have shown promise in treating both autoimmune diseases and ischemia/reperfusion injury. Conversely, soluble beta-glucan polysaccharides that bind to its lectin site prime the Mac-1/CR3 of circulating phagocytes and natural killer (NK) cells, permitting cytotoxic degranulation in response to iC3b-opsonized tumor cells that otherwise escape from this mechanism of cell-mediated cytotoxicity. CR3 binds soluble fungal β-glucan with high affinity ($5\times10^{-8}$ M) and this primes the receptor of phagocytes or NK cells for cytotoxic degranulation in response to iC3b-coated tumor cells. The tumoricidal response promoted by soluble β-glucan in mice was shown to be absent in mice deficient in either serum C3 (complement 3) or leukocyte CR3, highlighting the requirement for iC3b on tumors and CR3 on leukocytes in the tumoricidal function of β-glucans Vetvicka, V., et al., *J. Clin. Invest.* 98:50-61 (1996) and Yan, J., V. et al., *J. Immunol.* 163:3045-3052 (1999)).

Dectin-1 represents the second membrane receptor for β-glucan involved with glucan particle phagocytosis. Dectin-1 is expressed at high levels on thioglycolate-elicited peritoneal macrophages and its activity predominates over that of CR3 in the phagocytosis of yeast via β-glucan binding by these activated cells. However, yeast phagocytosis by neutrophils and resident peritoneal macrophages is blocked by anti-CR3 and does not occur with CR3-deficient (CD11b$^{-/-}$) neutrophils or resident macrophages. Moreover, dectin-1 is not expressed by NK cells that use CR3 to mediate tumoricidal activity against iC3b-opsonized mammary carcinoma cells following priming with β-glucan. Thus the role of dectin-1 in mediating β-glucan activities appears to be limited to activated peritoneal macrophages and perhaps also the intestinal CR3$^{-/-}$ macrophages observed to contain WGP-DTAF in this investigation.

The apparent need to administer β-glucans intravenously makes it unfeasible to consider use as a treatment for large numbers of people in emergency situations. Surprisingly, as described herein, orally administered WGP Beta Glucan functions to accelerate hematopoiesis following irradiation in an analogous manner as i.v. administered β-glucan, there is renewed interest in determining the mechanism and potential usefulness of β-glucan as a radioprotective drug for these types of nuclear emergencies.

The oral anti-infective and radiochemoprotective activities of a wide range of mushroom and yeast-derived β-glucans have been widely reported. As discussed above, the oral uptake of these high molecular weight β-glucans has been proposed via M cells in intestinal Peyer's patches. The results presented herein extend these observations to demonstrate that the oral uptake of whole glucan particles leads to β-glucan presentation to macrophages in the underlying GALT. These β-glucan-containing cells then transport the glucan into the organs of the reticuloendothelial system (lymph nodes, spleen and BM). This oral uptake and systemic distribution of WGP appears to be independent of the CR3-mediated mechanism of yeast particle phagocytosis, as there was the same uptake and distribution of WGP-DTAF in both wild-type and CR3$^{-/-}$ animals. The dectin-1 receptor, or other receptor can be responsible for this oral uptake of WGP into the GALT.

Of importance to explain the hematopoietic properties of oral WGP Beta Glucan treatment is the surprising discovery that daily feeding of WGP-DTAF leads to the appearance of WGP Beta Glucan-containing macrophages in the bone marrow (as shown in the Exemplification, Example 5). Two explanations for oral WGP Beta Glucan hematopoietic activity were considered: 1) WGP Beta Glucan breakdown and secretion of stimulatory soluble β-glucans that combine with deposited iC3b to stimulate stem cells via CR3, and 2) WGP Beta Glucan activation of macrophages to produce hematopoietic stimulatory cytokines such as GM-CSF.

Figure 2:
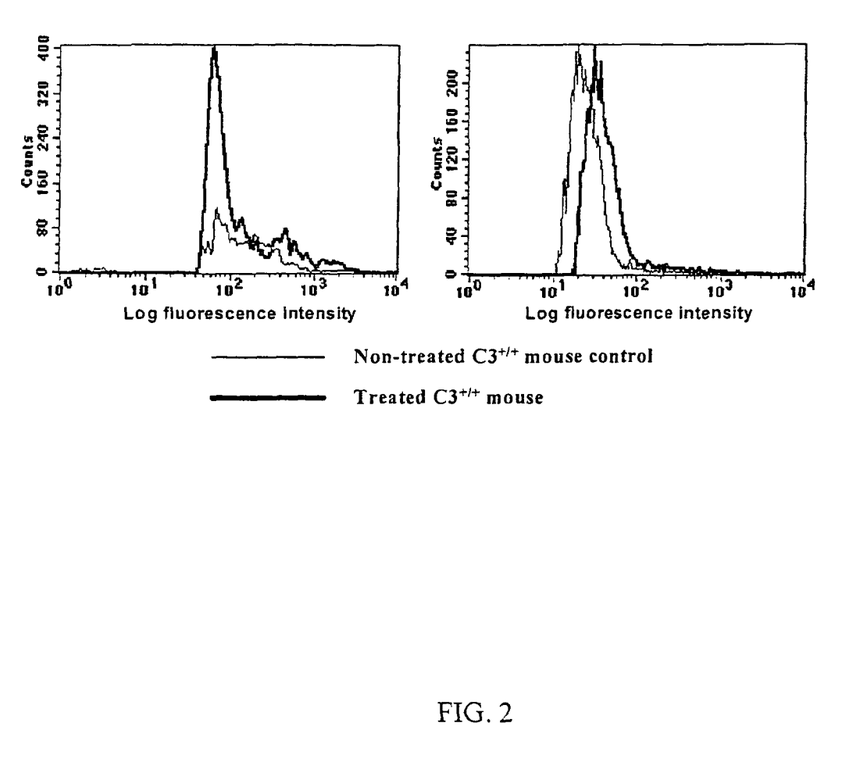
FIG. 2 graphically depicts histogram overlays showing net C3 staining after subtraction of background non-specific staining and compare marrow from treated versus untreated mice. Cyclophosphamide or sub-lethal radiation injury to bone marrow results in complement activaton with deposition of C3 on viable bone marrow cells. Normal or C3-deficient (C3−/−) mice were treated with either cyclophosphamide (200 mg/kg, left panel) or 3.0 Gy of total body gamma radiation (right panel) and then isolated marrow cells from treated versus untreated mice were analyzed for the presence of bound C3 by staining with goat anti-mouse C3-FITC and flow cytometry. Any staining of marrow cells from C3−/− mice with the anti-C3-FITC reagent was assumed to be non-specific and was subtracted from the total staining obtained with marrow cells from comparable treated or untreated wild-type (C3+/+) mice. With cyclophophamide, staining for C3 was observed on days 3 and 4 after treatment (day 4 shown). With irradiated mice, C3 staining was observed only at 24 (shown) and was not observed 3 days after radiation.

Macrophages that have ingested yeast cell walls or large soluble β-glucan molecules have been shown to degrade these materials and release small soluble fragments of β-glucan Examination by fluorescence microscopy of BM macrophages from animals fed WGP-DTAF for 7-12 days clearly showed evidence of WGP degradation (Example 5). Macrophage culture supernatants and lysates are currently being tested for biologically active β-glucan fragments using an assay that incorporates the limulus G-factor that agglutinates in response to picogram concentrations of soluble β(1,3)glucans. BM cells injured by gamma radiation or a cytotoxic drug (cyclophosphamide) that stimulated the activation of complement with deposition of iC3b on injured but still viable BM cells were also demonstrated (FIG. 2). Such cell-bound iC3b in combination with soluble β-glucan has been shown to activate the CR3 of mature myeloid cells, and in the BM may activate the CR3 of immature myeloid stem cells, causing accelerated hematopoiesis. Hematopoietic stem progenitor cells have been shown to express and to respond to soluble β-glucan in vitro. Also, supporting a putative role for soluble β-glucans released from macrophages are the previous reports showing that soluble β-glucans given i.v. can promote hematopoiesis in the same way as shown here with orally administered WGP Beta Glucan (Petruczenko, A., *Acta. Physiol. Pol.* 35:231-236 (1984) and Patchen, M. L. and T. J. MacVittie, *J. Biol. Response Mod.* 5:45-60 (1986)).

Figure 1:
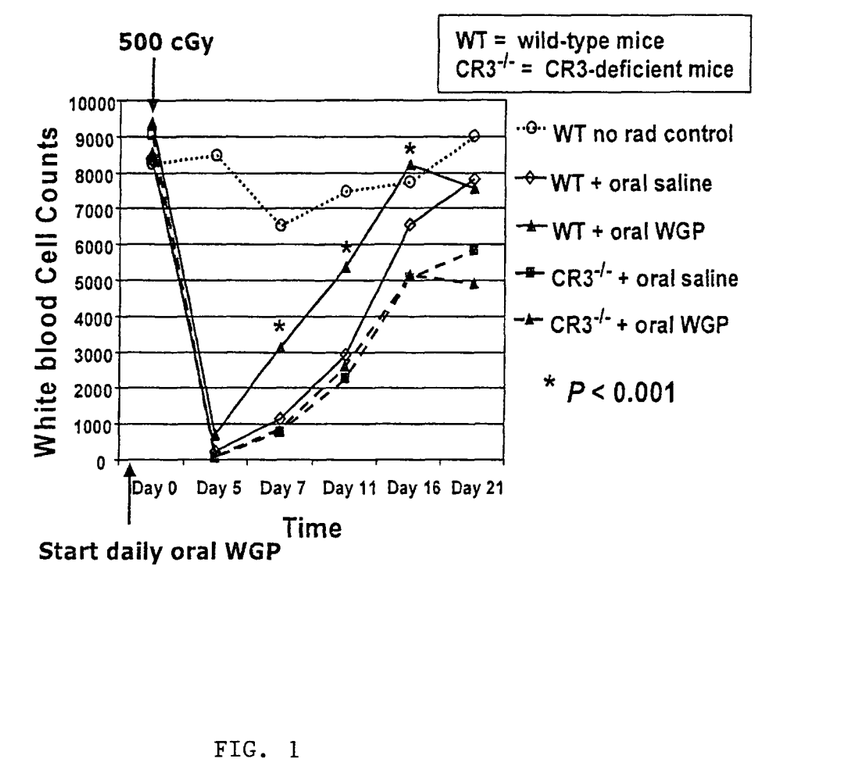
FIG. 1 graphically depicts a time course of white blood cell counts for wild type and CR3 deficient mice post a sublethal irradiation exposure.

A requirement for CR3 in mediating the enhanced hematopoietic affect of orally administered β-glucan is clearly evidenced by the failure of oral WGP Beta Glucan treatment to stimulate the recovery of WBC counts in $CR3^{-/-}$ animals following irradiation (FIG. 1). A direct role of CR3 in promoting hematopoiesis is supported by the observation that oral WGP-DTAF are efficiently taken up and transported to the BM in $CR3^{-/-}$ mice and yet these mice do not respond with an accelerated hematopoietic recovery in the same way as wild type mice. As outlined above, the role of CR3 could be mediated either through macrophages that are stimulated by WGP Beta Glucan to secrete hematopoietic cytokines only in wild-type and not in $CR3^{-/-}$ mice, or by the direct stimulation of $CR3^+$ hematopoietic cells through the co-stimulation by both the iC3b deposited on BM stromal cells and the soluble β-glucan released by macrophages that have ingested WGP Beta Glucan.

The Exemplification demonstrates the feasibility of using orally administered whole glucan particles as a therapeutic agent to protect individuals from the BM injury produced by exposure to gamma radiation. Orally administered whole glucan particles function through accelerating the normal process of hematopoiesis, making disease-fighting white blood cells available to the body several days sooner than would occur spontaneously. Orally administered whole glucan particles are bioavailable through their uptake by intestinal macrophages that transport it to the bone marrow and spleen. Based on these findings, two CR3-dependent mechanisms are described for the macrophage-ingested whole glucan particles to promote hematopoiesis. The invention described herein relates to methods of using an oral therapeutic to protect and treat individuals from harmful radiation exposure.

Preparation of WGP Glucan

Briefly, the process for producing the glucan particles involves the extraction and purification of the alkali-insoluble whole glucan particles from the yeast or fungal cell walls. This process yields a product, which maintains the morphological and structural properties of the glucan as, found in vivo, as is referred to as a whole glucan, or whole glucan particles. The structure-function properties of the whole glucan preparation depend directly on the source from which it is obtained and also from the purity of the final product. The source of whole glucan can be yeast or other fungi, or any other source containing glucan having the properties described herein. In certain embodiments, yeast cells are a preferred source of glucans. The yeast strains employed in the present process can be any strain of yeast, including, for example, *S. cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P ohmeri, Torulopsis bovin*, and *T. glabrata*.

Generally, the above procedure can be used to prepare and isolate other mutant yeast strains with other parent strains as starting material. Additionally, mutagens can be employed to induce the mutations, for example, chemical mutagens, irradiation, or other DNA and recombinant manipulations. Other selection or screening techniques may be similarly employed.

The yeast cells may be produced by methods known in the art. Typical growth media comprise, for example, glucose, peptone and yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid-to late logarithmic phase of growth, to minimize the amount of glycogen and chitin in the yeast cells. Glycogen, chitin and protein are undesirable contaminants that affect the biological and hydrodynamic properties of the whole glucan particles.

Preparation of whole glucan articles involves treating the yeast with an aqueous alkaline solution at a suitable concentration to solubilize a portion of the yeast and form an alkali-hydroxide insoluble whole glucan particles having primarily β(1,6) and β(1,3) linkages. The alkali generally employed is an alkali-metal hydroxide, such as sodium or potassium hydroxide or an equivalent. The starting material can comprise yeast separated from the growth medium. It is more difficult to control consumption of the aqueous hydroxide reactants and the concentration of reactants in the preferred ranges when starting with yeast compositions that are less concentrated. The yeast should have intact, unruptured cell walls since the preferred properties of the instant whole glucan particles depend upon an intact cell wall.

The treating step is performed by extracting the yeast in the aqueous hydroxide solution. The intracellular components and mannoprotein portion of the cell are solubilized in the aqueous hydroxide solution, leaving insoluble cell wall material which is substantially devoid of protein and having a substantially unaltered three dimensional matrix of β(1,6) and β(1,3) linked glucan. The preferred conditions of performing this step result in the mannan component of the cell wall being dissolved in the aqueous hydroxide solution. The intracellular constituents are hydrolyzed and released into the soluble phase. The conditions of digestion are such that at least in a major portion of the cells, the three dimensional matrix structure of the cell walls is not destroyed. In particular circumstances, substantially all the cell wall glucan remains unaltered and intact.

In certain embodiments, the aqueous hydroxide digestion step is carried out in a hydroxide solution having initial normality of from about 0.1 to about 10.0. Typical hydroxide solutions include hydroxides of the alkali metal group and alkaline earth metals of the Periodic Table. The preferred aqueous hydroxide solutions are of sodium and potassium, due to their availability. The digestion can be carried out at a temperature of from about 20° C. to about 121° C. with lower temperatures requiring longer digestion times. When sodium hydroxide is used as the aqueous hydroxide, the temperature can be from about 80° C. to about 100° C. and the solution has an initial normality of from about 0.75 to about 1.5. The hydroxide added is in excess of the amount required, thus, no subsequent additions are necessary.

Generally from about 10 to about 500 grams of dry yeast per liter of hydroxide solution is used. In certain embodiments, the aqueous hydroxide digestion step is carried out by a series of contacting steps so that the amount of residual contaminants such as proteins are less than if only one contacting step is utilized. In certain embodiments, it is desirable to remove substantially all of the protein material from the cell. Such removal is carried out to such an extent that less than one percent of the protein remains with the insoluble cell wall glucan particles. Additional extraction steps are preferably carried out in a mild acid solution having a pH of from about 2.0 to about 6.0. Typical mild acid solutions include hydrochloric acid, sodium chloride adjusted to the required pH with hydrochloric acid and acetate buffers. Other typical mild acid solutions are in sulfuric acid and acetic acid in a suitable buffer. This extraction step is preferably carried out at a temperature of from about 20° C. to about 100° C. The digested glucan particles can be, if necessary or desired, subjected to further washings and extraction to reduce the protein and contaminant levels. After processing the product pH can be adjusted to a range of about 6.0 to about 7.8.

By conducting this process without a step of disrupting the cell walls, the extraction can be conducted at more severe conditions of pH and temperature than was possible with the prior art procedure that included a step of disrupting the cell walls. That is, the process of this invention avoids product degradation while employing these severe extraction conditions which permits elimination of time-consuming multiple extraction steps.

After the above aqueous hydroxide treatment step, the final whole glucan product comprises about 5 to about 30 percent of the initial weight of the yeast cell, preferably the product is from about 7 to about 15 percent by weight.

The aqueous hydroxide insoluble whole glucan particles produced is as set forth in the summary of the invention. The whole glucan particles can be further processed and/or further purified, as desired. For example, the glucan can be dried to a fine powder (e.g., by drying in an oven); or can be treated with organic solvents (e.g., alcohols, ether, acetone, methyl ethyl ketone, chloroform) to remove any traces or organic-soluble material, or retreated with hydroxide solution, to remove additional proteins or other impurities that may be present.

In certain embodiments, the whole glucan particles obtained from the present process are comprised of pure glucan, which consists essentially of $\beta(1,6)$ and $\beta(1,3)$ linked glucan. The whole glucan particles contain very little contamination from protein and glycogen. In certain embodiments, the whole glucan particles are spherical in shape with a diameter of about 2 to about 10 microns and contain greater than about 85% by weight hexose sugars, (or in other embodiments greater than about 60% hexose sugars), approximately 1% by weight protein and no detectable amount of mannan, as determined monosaccharide analysis or other appropriate analysis. Glucans obtained by prior processes contain substantially higher quantities of chitin and glycogen than the present glucans.

The second step as set forth above, involves the modification of the whole glucan particles, as produced above, by chemical treatment to change the properties of the glucan. It is contemplated that whole glucan particles derived from any yeast strain may be used, in addition to those particular strains described herein. As mentioned above, a very broad spectrum of yeast or mutant yeast strains may be used. The processing conditions described above are also applicable to glucan extraction from fungi in general. The properties of these glucans also will depend on the sources from which they are derived.

According to a first chemical treatment, the whole glucan particles can be treated with an acid to decrease the amount of $\beta(1,6)$ linkages and thus, change the hydrodynamic properties of said glucans as evidenced by an increase in the viscosity of aqueous solutions of these modified glucans.

A process for preparing an altered whole glucan particles by treating the glucan particles with an acid, for a suitable period of time to alter the $\beta(1,6)$ linkages can also be used. Acetic acid is preferred, due to its mild acidity, ease of handling, low toxicity, low cost and availability, but other acids may be used. Generally these acids should be mild enough to limit hydrolysis of the $\beta(1,3)$ linkages. The treatment is carried out under conditions to substantially only affect the $\beta(1,6)$ linked glucans. In certain embodiments, the acid treatment is carried out with a liquid consisting essentially of acetic acid, or any dilutions thereof (typical diluents can be organic solvents or inorganic acid solutions). The treatment is carried out at a temperature of from about 20° C. to about 100° C. In certain embodiments, the treatment is carried out to such an extent to remove from about 3 to about 20 percent by weight of acid soluble material based on total weight of the whole glucan particles before treatment. In other embodiments, the extent of removal is from about 3 to about 4 percent by weight. Certain compositions formed demonstrate altered hydrodynamic properties and an enhancement in viscosity after treatment.

According to a second chemical treatment, the whole glucan particles are treated with an enzyme or an acid, to change the amount of $\beta(1,3)$ linkages. For whole glucan particles derived from some yeast strains, enzyme treatment causes a decrease in the viscosity, and for others, it causes an increase in viscosity, but in general, alters the chemical and hydrodynamic properties of the resulting glucans. The treatment is with a $\beta(1,3)$ glucanase enzyme, such as laminarinase, for altering the $\beta(1,3)$ linkages to alter the hydrodynamic properties of the whole glucan particles in aqueous suspensions.

The enzyme treatment can be carried out in an aqueous solution having a concentration of glucan of from about 0.1 to about 10.0 grams per liter. Any hydrolytic glucanase enzyme can be used, such as laminarinase, which is effective and readily available. The time of incubation may vary depending on the concentration of whole glucan particles and glucanase enzyme. The $\beta(1,3)$ linkages are resistant to hydrolysis by mild acids such as acetic acid. Treatment with strong or concentrated acids, such as hydrochloric acid (HCl), sulfuric acid ($H_2SO_4$) or formic acid, hydrolyzes the $\beta(1,3)$ linkages thereby reducing the amount of $\beta(1,3)$ linkages. The acid treatment can be carried out in an aqueous solution having a concentration of glucan from about 0.1 to about 10.0 grams per liter. The time of acid treatment may vary depending upon the concentration of whole glucan particles and acid. Acid hydrolysis can be carried out at a temperature of from about 20° C. to about 100° C. The preferred compositions formed demonstrate altered hydrodynamic properties.

By controlling the incubation time, it is possible to control the chemical and hydrodynamic properties of the resulting product. For example, the product viscosity can be precisely controlled for particular usage, as, for example, with a variety of food products.

A hydrodynamic parameter ($K_1$) of the final treated product having altered linkages is dependent on the treatment time according to the final formula:

$$K_1 = -0.0021(\text{time}) + 0.26$$

where time is in minutes; and
where time is less than one hour.

The parameter $K_1$ is directly related (proportional) to the relative viscosity. In the case of aqueous suspensions the relative viscosity is equal to the actual viscosity when the latter is measured in centipoise.

A process for preparing aqueous slurry of a glucan having a predetermined desired viscosity is provided. The slurry comprises glucan at a concentration that is a function of the predetermined desired viscosity according to the following approximate formula:

$$1/\text{concentration} = K_1 \times (1/\log(\text{relative viscosity})) + K_2$$

Where,
$K_1$ = (shape factor) × (hydrodynamic volume); and
$K_2$ = (hydrodynamic volume)/(maximum packing fraction).

The shape factor is an empirically determined value that describes the shape of the glucan matrix in its aqueous environment. The shape factor is a function of the length:width ratio of a particle and can be determined microscopically. The hydrodynamic volume is a measure of the volume a particle occupies when in suspension. This is an important parameter for glucan suspensions in that it indicates the high water holding capacity of glucan matrices. The maximum packing fraction can be described as the highest attainable volume fraction of glucans that can be packed into a unit volume of suspension.

Preparation of Microparticulate β-Glucan Particles

Beta (1,3) glucan starting material can be isolated from yeast cell walls by conventional methods known by those of ordinary skill in the art. The general method for the production of glucan from yeast involves extraction with alkali followed by extraction with acid (Hassid et al., *Journal of the American Chemical Society*, 63:295-298, 1941). Improved methods for isolating a purified water insoluble beta (1,3) glucan extract are disclosed in U.S. Pat. No. 5,223,491, which is incorporated herein by reference in its entirety. Methods for preparing microparticulate β-glucan particles are disclosed in U.S. Pat. No. 5,702,719, the disclosure of which is incorporated herein by reference in its entirety. An improved microparticulate glucan product is obtained when the average particle size is preferably about 1.0 microns or less, and more preferably about 0.20 microns or less.

To obtain the desired smaller particle size, the mixture comprising the beta (1,3) glucan product is ground down using a blender, microfluidizer, or ball mill, for example. One grinding or particle size reduction method utilizes a blender having blunt blades, wherein the glucan mixture is blended for a sufficient amount of time, preferably several minutes, to completely grind the particles to the desired size without overheating the mixture. Another grinding method comprises grinding the glucan mixture in a ball mill with 10 mm stainless steel grinding balls. This latter grinding method is particularly preferred when a particle size of about 0.20 microns or less is desired.

Prior to grinding, the glucan mixture is preferably passed through a series of sieves, each successive sieve having a smaller mesh size than the former, with the final mesh size being about 80. The purpose of sieving the mixture is to separate the much larger and more course glucan particles from smaller particles (the pore size of an 80 mesh sieve is about 0.007 inches or 0.178 mm). The separated larger particles are then ground down as described above and re-sieved to a final mesh size of 80. The process of sieving and grinding is repeated until a final mesh size of 80 is obtained. The sieved particles are combined and ground down further, preferably for at least an hour, until the desired particle size is obtained, preferably about 1.0 micron or less, more preferably about 0.20 microns or less. Periodic samples of the fine grind glucan are taken during the grinding process and measured using a micrometer on a microscope.

Formulation

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g., PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein in its entirety. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

EXEMPLIFICATION

Materials and Methods for Examples 1-4

Bioavailability of WGP Glucan

The in vivo fate of oral yeast β-glucan particles (GP) was explored using GP-fluorescein (GP-F). Gastrointestinal macrophages shuttled GP-F to lymphoid tissues, with GP-F appearing within splenic macrophages 3 days after oral administration and within bone marrow (BM) macrophages after 5 days. CR3 was not required for macrophage uptake of GP-F, as BM macrophages from both wild-type and $CD11b^{1/!}$ mice contained GP-F. BM macrophages digested GP-F and secreted soluble β-glucan-F that was bound/coated by BM neutrophils via CR3. Only neutrophils elicited from mice that had been given oral GP were able to kill iC3b-opsonized tumor cells.

Oral Prophylaxis Using WGP Glucan.

Oral prophylaxis with WGP glucan using 0.1 ml of a 0.1-100 mg/ml suspension was administered per mouse by oral gavage. The WGP glucan suspension was prepared in sterile water with vigorous agitation for at least 1 hour. The suspension can be aliquoted and stored frozen for up to 1 year, or at 4° C. for up to 1 week. Before use, the suspension was mixed vigorously to ensure a uniform suspension. Note, the WGP glucan suspension will settle out in the syringe, so the contents of the syringe are mixed by inversion to ensure a uniform suspension. The controls are then treated with a 0.1 ml gavage of water.

Alternatively, the WGP glucan can be dosed in the animal's drinking water at a concentration of 20 μg/ml. To maintain an even suspension, the WGP glucan suspension is prepared in 0.3% carboxymethylcellulose. The control animals are treated with 0.3% carboxymethylcellulose control water.

The recommended prophylactic oral schedule is daily gavage on days −7 to 0. Irradiation by exposure to $^{60}$Co radiation was administered 1-3 hours post final prophylactic dose.

Parenteral Prophylaxis Using WGP Glucan.

Parenteral prophylaxis with WGP glucan using 0.1 ml of a 0.1-100 mg/ml suspension was administered per mouse by subcutaneous, intramuscular, intradermal or intraperitoneal injection. The WGP glucan suspension is normally prepared in sterile physiological saline with vigorous agitation for at least 1 hour. The suspension can be aliquoted and stored frozen for up to 1 year, or at 4° C. for up to 1 week. Before use, the suspension is mixed vigorously to ensure a uniform suspension. Note, the WGP glucan suspension settles out in the syringe, so the contents of the syringe are mixed by inversion to ensure a uniform suspension. The controls are then injected with a 0.1 ml sterile physiological saline. Irradiation for 1-3 hours is administered after final prophylactic dose.

Oral Therapeutic Use of WGP Glucan.

Oral therapeutic treatment with WGP glucan using 0.1 ml of a 0.1-100 mg/ml suspension was administered per mouse by oral gavage. The WGP glucan suspension is prepared in sterile water with vigorous agitation for at least 1 hour. The suspension can be aliquoted and stored frozen for up to 1 year, or at 4° C. for up to 1 week. Before use, the suspension was mixed vigorously to ensure a uniform suspension. Note, the WGP glucan suspension settles out in the syringe, so the contents of the syringe are mixed by inversion to ensure a uniform suspension.

Alternatively, the WGP glucan can be dosed in the animal's drinking water at a concentration of 200 μg/ml. To maintain an even suspension, the WGP glucan suspension is prepared in 0.3% carboxymethylcellulose. Control animals are treated with 0.3% carboxymethylcellulose control water.

The oral therapeutic dosing schedule is daily gavage on days 0-10, providing the first dose 1 hour after infection. Alternatively, the glucan dose is provided in the drinking water starting 1 hour after irradiation.

Parenteral Therapeutic Use of WGP Glucan.

Parenteral therapeutic treatment with WGP glucan using 0.1 ml of a 0.1-100 mg/ml suspension is administered per mouse by subcutaneous, intramuscular, intradermal, intravenous or intraperitoneal injection. The WGP glucan suspension is generally prepared in sterile physiological saline with vigorous agitation for at least 1 hour. The suspension can be aliquoted and stored frozen for up to 1 year, or at 4° C. for up to 1 week. Before use, the suspension is mixed vigorously to ensure a uniform suspension. Note, the WGP glucan suspension settles out in the syringe, so the contents of the syringe are mixed by inversion to ensure a uniform suspension. The controls are treated with a 0.1 ml injection of physiological saline. The parenteral therapeutic dosing schedule is injections on days 0, 1, 3, 5, 7, and day 9. The first dose is provided 1 hour after irradiation.

Combined Prophylactic and Therapeutic Oral Treatment

Oral prophylactic and therapeutic treatment with WGP glucan using 0.1 ml of a 0.1-100 mg/ml suspension is administered per mouse by oral gavage. The WGP glucan suspension is prepared in sterile water with vigorous agitation for at least 1 hour. The suspension can be aliquoted and stored frozen for up to 1 year, or at 4° C. for up to 1 week. Before use, the suspension is mixed vigorously to ensure a uniform suspension. Note, the WGP glucan suspension settles out in the syringe, so the contents of the syringe are mixed by inversion to ensure a uniform suspension. The controls are treated with a 0.1 ml gavage of water.

Alternatively, the WGP glucan is dosed in the animal's drinking water at a concentration of 20 μg/ml. To maintain an even suspension, the WGP glucan suspension is prepared in 0.3% carboxymethylcellulose. The control animals are treated with 0.3% carboxymethylcellulose control water.

The oral prophylactic and therapeutic dosing schedule is daily gavage on day −7 to day +10 and the first dose is provided 1 hour after irradiation.

Example 1

This example concerns the intravenous administration of WGP obtained using the described procedure from *S. cerevisiae* to mice to observe radioprotectant activity. WGP was suspended in sterile saline by placing it in a sonicating water bath at room temperature for 30 minutes to produce a fine suspension. Alternately, The WGP can be passed through a syringe needle of decreasing diameter until the material is capable of passing through the needle used for tail vein injection. A 4.0 mg/ml solution prepared in this fashion was administered to a group of 20 wild type C57B1/6 mice 1 day before irradiation with 6.5 Gy $^{60}$Co radiation by injecting 0.1 ml of the suspension into the tail vein. Survival rates of the treated mice changed dramatically over days 10 to 15 post-irradiation. Thirty days post-irradiation, 51% of the glucan treated mice were alive, while in control experiments, none of the mice survived beyond 21 days post-irradiation.

Example 2

This example concerns the oral administration of WGP obtained using the described procedure from *S. cerevisiae* to mice to observe radioprotectant activity. WGP was suspended in sterile saline by passing it through a gavage needle to ensure the elimination of lumps of material. A 0.8 mg/ml suspension prepared in this fashion was administered to a group of 20 wild type C57B1/6 mice 1 day before irradiation with 6.5 Gy $^{60}$Co radiation by gavaging the suspension. Dosing was continued ever day up to 10 days after irradiation. Survival rates of the treated mice were the same as that observed with intravenous administration. Thirty days post-irradiation, 51% of the glucan treated mice were alive, while in control experiments, none of the mice survived beyond 21 days post-irradiation.

Example 3

This example concerns the intravenous administration of WGP obtained using the described procedure from *S. cerevisiae* to mice to observe the stimulation of post-radiation myelosuppressive recovery. WGP was suspended in sterile saline by placing it in a sonicating water bath at room temperature for 30 minutes to produce a fine suspension. Alternately, The WGP can be passed through a syringe needle of decreasing diameter until the material is capable of passing through the needle used for tail vein injection. A 4.0 mg/ml solution prepared in this fashion was administered to a group of 5 wild type C57B1/6 mice 1 day before irradiation with a nonfatal 650-rad dose of total-body gamma radiation by injecting 0.1 ml of the suspension into the tail vein. Myelosuppression recovery, as indicated by white blood cell (WBC) count, had diverged 7 days post-irradiation, as shown on the chart below, with mice treated with WGP showing significantly higher white blood cell counts than mice treated with saline.

Example 4

This example concerns the intravenous administration of WGP obtained using the described procedure from *S. cerevisiae* to mice following carboplatinum treatment to demonstrate myelosuppressive recovery. WGP was suspended in sterile saline by placing it in a sonicating water bath at room temperature for 30 minutes to produce a fine suspension. Alternately, The WGP can be passed through a syringe needle of decreasing diameter until the material is capable of passing through the needle used for tail vein injection. A 4.0 mg/ml solution prepared in this fashion was administered to a group of 5 wild type C57B1/6 mice 1 day after treatment with 115 mg/Kg carboplatinum by injecting 0.1 ml of the suspension into the tail vein. Myelosuppression, as indicated by white blood cell (WBC) count, occurred between 8 and 10 days after carboplatinum treatment. WBC counts of treated mice began to recover 13 days after carboplatinum administration, showing $5 \times 10^6$ WBC/ml by day 13 and $12 \times 10^6$ WBC/ml by day 17. Untreated mice began recovery a day later than treated mice, and showed WBC levels consistently lower than treated mice by about $5 \times 10^6$ WBC/ml.

Example 5

In Vivo Uptake of Oral Beta Glucan

Materials and Methods
Animals.

A colony of CR3-deficient ($CD11^{-/-}$) mice and their wild-type littermates on a C57BL/6 background was established at the University of Louisville from breeders provided by Dr. Tanya Mayadas (Harvard Medical School, Boston, Mass.) who had generated the founder mice Coxon, A., et al., *Immunity*, 5:653-666 (1996)). Another colony of mice deficient in the serum complement protein C3 ($C3^{-/-}$) and their wild-type littermates on a C57BL6 background was established from heterozygous breeders obtained from the Jackson Laboratory (Bar Harbor, Me.) that came originally from founder mice generated by Dr. Michael Carroll (Center for Blood Research, Harvard Medical School, Boston, Mass.) (Wessels, M. R. et al., *Proc. Natl. Acad. Sci. USA* 92:11490-11494 (1995)). Mice used for these experiments were all 10 weeks of age, and equal numbers of males and females were examined.

Immune Modulators

WGP Beta Glucan (WGP, WG™ Beta Glucan (Imucell™), Biopolymer Engineering Inc., Eagan, Minn., USA) is a component from the cell walls of Baker's yeast that is purified by extraction of cellular proteins, nucleic acids, lipids, and most non-glucose-based oligosaccharides (e.g., chitin and mannans) by a morphologically non-destructive proprietary process as described by U.S. Pat. No. 5,504,079. It is a highly purified, 3-5 micron, spherical β-glucan particle. WGP Beta Glucan was labeled with fluorescein using DTAF (Molecular Probes, Inc., Oregon) generating a green WGP-DTAF particle for fluorescence microscopy or flow cytometry.

WGP Absorption and Distribution

Using WGP-DTAF, phagocytosis was measured by flow cytometry and cells isolated with ingested WGP-DTAF by fluorescence-activated cell sorting (FACS). To monitor the uptake of orally administered WGP-DTAF, mice were fed 400 μg of the WGP-DTAF daily by intragastric administration and then examined on days 3, 7, and 12 for the presence of splenic, lymph node, and BM macrophages containing WGP-DTAF by FACS and fluorescence microscopy. Macrophages containing green WGP-DTAF were identified by red surface staining with the macrophage-specific antibody F4/80 coupled to the red fluorochrome, cychrome 5 (i.e., Cy5, BD Biosciences Pharmingen, San Diego, Calif.).

Radiation Protection

To test the radiation protective effects of oral WGP Beta Glucan treatment, groups of 5 mice, either wild-type or $CR3^{-/-}$ mice, were given either an intragastric dose of 80 µg of WGP suspended in saline or saline only (control) one day prior to a sublethal radiation exposure (500 cGy). The mice received additional daily intragastric doses of WGP Beta Glucan or saline control for the entire 3-week period of observation. Other groups of wild-type or $CR3^{-/-}$ mice received a single i.v. injection of 400 µg of WGP Beta Glucan suspension in saline or saline control one day prior to radiation. A control wild-type group received no irradiation. White blood cell (WBC) counts were determined periodically over a 3-week observation period for each mouse and FACS was carried out to determine the proportions of granulocytes (Gr-$1^{high}$), monocytes (Gr-$1^{low}$), T cells ($CD3^+$) and B cells ($CD19^+$). Numerical count data were evaluated using Prism 3.0 (Graph Pad Software, San Diego, Calif.) that calculated the mean, standard deviation, and statistical significance (Student's T test) of values obtained from the individual groups of mice at each time point.

Cytokine Synthesis.

White blood cell cytokine synthesis was evaluated by intracytoplasmic staining of specific cytokines (IL-4, IL-6, IL-12, tumor necrosis factor (TNFα), IFNγ, and GM-CSF) using a test kit (BD Biosciences Phamingen) in which specific leukocyte types were labeled by surface staining and then the leukocytes were permeabilized for cytoplasmic staining using fluorochrome-labeled antibodies to specific cytokines. The stained leukocytes were examined by flow cytometry, and the specificity of cytoplasmic staining was evaluated by showing blockade of fluorochrome-labeled antibody staining with an excess of homologous unlabeled antibody. This test was applied to mouse blood leukocytes or peritoneal leukocytes from wild-type or $CR3^{-/-}$ mice at various times after administration of WGP Beta Glucan by intragastric or intraperitoneal dosing. Cytokine secretion was evaluated in isolated human blood monocytes incubated in vitro with WGP Beta Glucan using an ELISA assay as described in *Immunopharmacology*, 42:61074 (1999).

C3 Deposition on Bone Marrow Stroma.

To determine if complement was activated by damage to bone marrow (BM) cells produced by radiation or cyclophosphamide, the BM of mice treated with these agents was removed and the isolated and washed BM cells were stained with rabbit anti-mouse C3c-FITC. The presence of bound C3 (iC3b fragment) on viable cells was evaluated by flow cytometry by gating on viable cells that were not stained with propidium iodide.

Results

Parallel research on the ability of β-glucans to promote tumoricidal and anti-infective activities indicated that orally administered yeast-derived WGP Beta Glucan was equally effective as β-glucans given intravenously (i.v.). Since, i.v. administered β-glucans have been shown to promote hematopoiesis and to protect mice from lethal gamma radiation injury, experiments were designed to determine if orally administered WGP Beta Glucan was equally effective as β-glucans given i.v.

Orally Administered WGP are Bioavailable.

In vitro tests with resident peritoneal macrophages and the J774 murine macrophage cell line showed that the fluorescein label on WGP-DTAF did not alter the biological activities or CR3 specificity of macrophage phagocytosis. Following 3-12 days of WGP-DTAF feeding to mice, cells containing WGP-DTAF were detected in spleen, peritoneal lymph nodes, and BM. FACS sorting of the fluorescein-positive cells allowed examination of cells by fluorescence microscopy. Microscopic visualization confirmed that the green fluorescence corresponded to ingested WGP-DTAF particles within cells, and that all cells containing green WGP-DTAF were also stained red with the macrophage specific antibody F4/80-Cy5. Although no WGP-DTAF were detected in macrophages from $CR3^{-/-}$ mice on day 3, approximately equivalent numbers of WGP-DTAF containing macrophages were detected in all lymphoid organs examined from $CR3^{-/-}$ versus wild-type mice on days 7 and 12.

Macrophages that have ingested yeast cell walls or large soluble β-glucan molecules degrade these materials and release small soluble fragments of β-glucan. Microscopic evaluation of WGP-DTAF in macrophages isolated from BM or spleen showed the presence of intact and spherical WGP-DTAF particles early after feeding, whereas the particles appeared more fragmented and diffuse in BM macrophages isolated 7-12 days after feeding DTAF-WGP. These results demonstrate that WGP Beta Glucan is orally bioavailable and that the WGP Beta Glucan-containing intestinal macrophages migrate to BM, spleen, and lymph nodes where the WGP are degraded in situ into smaller fragments of β-glucan, which can be responsible for the hematopoeitic activity of oral WGP.

Oral WGP Beta Glucan Protects Against Radiation Damage

In irradiated mice, WBC counts reached a nadir of <1,000 per $mm^3$ on day 5, and WBC counts returned to normal on day 21 in irradiated wild-type mice treated with i.v. or oral saline (FIG. 1). In wild-type mice receiving intravenous administration WGP, WBC counts were higher than intravenous administration of saline controls on day 7 only. In comparison, wild-type mice given WGP Beta Glucan orally exhibited significantly higher WBC counts than did mice given oral saline on days 7, 11, and 16 after irradiation and returned to normal 5 days sooner than mice receiving oral or i.v. saline (i.e., day 16 vs. 21) and 3 days sooner than mice receiving a single dose of i.v. WGP Beta Glucan. It is particularly noteworthy that the saline-treated $CR3^{-/-}$ mice exhibited a significantly slower hematopoietic reconstitution than did the saline-treated wild-type mice, and that there was no enhancement of recovery induced by oral (FIG. 1) or i.v. WGP Beta Glucan. Flow cytometry analysis showed equivalent recovery of each of the major leukocyte types examined in the WGP Beta Glucan-treated mice as compared to the saline-treated mice.

Damage to Marrow Caused by Radiation, Cyclophosphamide, or G-CSF Activates Complement and Deposits iC3b on Viable Marrow Stromal Cells Following BM injury, hematopoietic stem progenitor cells (HSPC) home to the site of marrow injury and attach to the injured cells prior to initiating the repair process. Attachment of HSPC to the site of marrow injury may involve CR3 that is expressed on the membranes of HSPC and can function as an adhesion molecule to allow HSPC attachment to stromal cells. HSPC that lack CR3 fail to attach to the BM and initiate hematopoiesis. A major ligand for CR3 that could mediate such attachment is the iC3b fragment of C3 that can become attached to injured tissues through activation of the complement system. As described herein, BM cells from normal but not C3$^{-/-}$ mice exposed to gamma radiation or cyclophosphamide had surface deposits of the iC3b on injured (but still viable cells) that was detectable by immunofluorescence staining and flow cytometry (FIG. 2). The attachment of HSPC via CR3 to this iC3b deposited on BM cells has been suggested by the finding of enhanced release of HSPC from the BM into the blood of either normal mice treated with a blocking antibody to CR3 or mice genetically deficient in CR3 or C3. Attachment of HSPC to this iC3b on injured BM cells in the presence of soluble β-glucan (released from macrophages that have ingested WGP) can provide a signal that activates the HSPC for enhanced hematopoiesis. For example, the activation of mature myeloid cells by soluble β-glucan requires the co-stimulation of CR3 by membrane-bound (deposited) iC3b.

Stimulation of Cytokine Synthesis

Analysis of murine peritoneal macrophages by intracellular staining and flow cytometry demonstrated that macrophages stimulated by WGP Beta Glucan phagocytosis in vivo synthesized TNFα, IL-6, IL-12, and GM-CSF (data not shown). Notably, these cytokines were detected only in macrophages from wild-type but not from CR3$^{-/-}$ mice that were isolated 24 h after intraperitoneal injection of WGP Beta Glucan. The only change in cytokines observed among blood leukocytes from mice given daily intragastric doses of WGP Beta Glucan for 6 days was that there was a significant increase in the proportion of CD4$^+$ helper T cells containing the Th1 cytokine IFNγ (increased from 0.5% to 3.5%). This finding may be due to the presence of WGP Beta Glucan-stimulated macrophages in lymph nodes that secreted IL-12, a cytokine that stimulates the formation of Th1 cells. ELISA assays of human blood monocytes similarly demonstrated that ingestion of WGP Beta Glucan stimulated the secretion of TNFα, IL-6, and IL-12. Thus, it is likely that the WGP Beta Glucan-containing intestinal macrophages that migrate to BM secrete these cytokines and that these cytokines may contribute to action of oral WGP Beta Glucan in stimulating hematopoiesis.

Example 6

All materials and methods are the same as Example 1 except where noted.

Animals

C3aR^-/- mice Dr. Rich Wetsel, Unviversity of Texas, Houston, can be produced using methods standard in the art, such as those described in A. Wetsel. 1998. Cloning, expression, sequence determination, and chromosome localization of the mouse complement C3a anaphylatoxin receptor gene. *Mol. Immunol.* 35:137.

C3 Deposition on Bone Marrow Stroma

To determine if complement was activated by damage to bone marrow (BM) cells produced by radiation or cyclophosphamide, the BM of mice treated with these agents was removed and the isolated and washed BM cells were stained with rabbit anti-mouse C3c-FITC. The presence of bound C3 (iC3b fragment) on viable cells was evaluated by flow cytometry by gating on viable cells that were not stained with propidium iodide.

C3 goes to a and B, A is used for homing C3Ar, chemotaxis is also enhanced with glucan.

Results

In addition to its functions in immunity, the C system also stimulates inflammation and promotes clearance of dead or apoptotic cells. Moreover, in ischemia/reperfusion injury, a neoantigen becomes exposed on hypoxia-injured tissue that reacts with an IgM natural antibody, thereby activating the classical pathway of C and releasing C3a that recruits C3aR^+ mast cells and C5a that recruits CR3 (iC3b-receptor; CD11b/CD18)^+ neutrophils that become tethered via iC3b deposited on the injured tissue. This investigation showed that iC3b was deposited within 24 hr onto BM cells from mice given 5.0 Gy of gamma radiation. The iC3b was detected by flow cytometry with anti-C3c-FITC on viable cells (propidium iodide-negative), but was absent on BM cells from irradiated C3^-/- mice. A function for BM-bound iC3b was suggested because of delayed recovery of WBC counts following radiation of C3^-/- mice as compared to wild-type mice. A similarly delayed WBC recovery also occurred with both CD11b^-/- mice and C3aR^-/- mice, suggesting roles for both CR3 and C3aR, both of which are expressed on hematopoietic stem progenitor cells (HSPC). In addition, C3aR^-/- mice exhibited a delayed recovery of RBC counts and a deficit in erythrocyte stem progenitor cells (BFU-E). CR3 was further implicated in myeloid HSPC function by the finding that orally administered whole yeast 13-glucan particles (WGP) induced a significant increase in WBC (but not RBC) recovery (16 days vs. 21 days) in irradiated wild-type but not CD11b^-/- mice. Orally administered WGP-fluorescein was taken up by gastrointestinal macrophages that conveyed it to the BM and spleen where the macrophages released soluble β-glucan fragments (shown to prime CR3^+HSPC in vitro) and secreted inflammatory cytokines including IL-12. Because ligation of β-glucan-primed CR3^+ myeloid cells to iC3b-coated cells is an activation signal, it is proposed that soluble β-glucan released in the BM by macrophages functions to prime the CR3 of HSPC that have been tethered to the iC3b deposited onto BM cells, thereby enhancing the normal rate of HSPC expansion and differentiation. The oral WGP preparation as described herein can be a therapeutic given to individuals at risk for exposure to harmful radiation as the result of a nuclear power plant accident or nuclear terrorism. These data indicate an important role in hematopoiesis of both the C3a-C3aR axis and the iC3b-CR3 receptor axis, and do not exclude the participation of other components or receptors.

Those skilled in the art will recognize, or be able to ascertain using no more than routine experimentation, many equivalents to the specific embodiments of the invention described specifically herein Such equivalents are intended to be encompassed in the scope of the following claims.

What is claimed is:

1. A method of treating injury from ionizing radiation, chemotherapy, or a combination of radiation and chemotherapy, the method comprising administering to an individual an effective amount of an unmodified particulate, bioavailable β(1,3; 1,6) glucan formulation.

2. The method of claim 1 wherein said unmodified particulate, bioavailable β(1,3; 1,6) glucan formulation comprises whole glucan particles, microparticulate β-glucan particles, or a combination of whole glucan particles and microparticulate β-glucan particles.

3. The method of claim 2 wherein whole glucan particles have a diameter of 1 micron or greater.

4. The method of claim 2 wherein the microparticulate β-glucan particles have a diameter of 1 micron or less.

5. The method of claim 2 wherein the whole glucan particles, microparticulate β-glucan particles, or a combination of whole glucan particles and microparticulate β-glucan particles are administered orally.

6. The method of claim 5 wherein a therapeutically effective dose of no more than about 100 mg/kg of body weight is administered daily.

7. A method of treating myelosuppression, the method comprising administering to an individual an effective amount of an unmodified particulate, bioavailable β(1,3; 1,6) glucan.

8. The method of claim 7 wherein the myelosuppression is caused by ionizing radiation.

9. The method of claim 7 wherein the myelosuppression is caused by chemotherapy.

10. The method of claim 7 wherein said unmodified particulate, bioavailable β(1,3; 1,6) glucan formulation comprises whole glucan particles, microparticulate β-glucan particles, or a combination of whole glucan particles and microparticulate β-glucan particles.

11. The method of claim 10 wherein whole glucan particles have a diameter of 1 micron or greater.

12. The method of claim 10 wherein the microparticulate β-glucan particles have a diameter of 1 micron or less.

13. The method of claim 10 wherein the whole glucan particles, microparticulate β-glucan particles, or a combination of whole glucan particles and microparticulate β-glucan particles are administered orally.

14. The method of claim 12, wherein a therapeutically effective dose of no more than about 100 mg/kg of body weight is administered daily.

15. A method of treating the reduction of macrophage activity created by radiation or chemotherapy, the method comprising administering to an individual an effective amount of an unmodified particulate, bioavailable β(1,3; 1,6) glucan.

16. A method of enhancing glucan-mediated hematopoietic progenitor stem cell recovery after exposure to radiation via the complement system, the method comprising administering to an individual an effective, orally bioavailable amount of unmodified whole glucan particles, wherein the glucan activates the complement system and enhances regeneration of hematopoietic progenitor stem cells.

17. The method of claim 16, wherein the orally administered unmodified glucan is taken up by macrophages, transported to the bone marrow, degraded and the released fragments prime the CR3 of stem cell activating the stem cells to differentiate and proliferate.

18. The method of claim 17, wherein the β(1,3; 1,6) glucan via the complement system promotes stem cell proliferation and differentiation by binding to iC3b deposited on injured stem cells and activating CR3.

19. The method of claim 1 wherein the unmodified particulate, bioavailable β(1,3; 1,6) glucan formulation is administered to the individual before the ionizing radiation, chemotherapy, or combination of radiation and chemotherapy.

20. The method of claim 1 wherein the unmodified particulate, bioavailable β(1,3; 1,6)glucan formulation is administered to the individual after the ionizing radiation, chemotherapy, or combination of radiation and chemotherapy.

21. The method of claim 7 wherein the unmodified particulate, bioavailable β(1,3; 1,6) glucan is administered to the individual before onset of the myelosuppression.

22. The method of claim 7 wherein the unmodified particulate, bioavailable β(1,3; 1,6) glucan is administered to the individual after onset of the myelosuppression.

23. The method of claim 15 wherein the unmodified particulate, bioavailable β(1,3; 1,6) glucan is administered before the radiation or chemotherapy.

24. The method of claim 15 wherein the unmodified particulate, bioavailable β(1,3; 1,6) glucan is administered after the radiation or chemotherapy.

25. The method of claim 16 wherein the unmodified whole glucan particles are administered before the individual is exposed to the radiation.

26. The method of claim 16 wherein the unmodified whole glucan particles are administered before the individual is exposed to the radiation.

* * * * *